United States Patent [19]

Albarella et al.

[11] Patent Number: 5,696,264
[45] Date of Patent: Dec. 9, 1997

[54] FOLATE-ALP CONJUGATE

[75] Inventors: James P. Albarella, Granger; Linda M. Anderson-Mauser, Elkhart, both of Ind.; Frank Thomas Hartl, Chestnut Ridge, N.Y.; Gary M. Johnson, Elkhart, Ind.

[73] Assignee: Bayer Corporation, Elkhart, Ind.

[21] Appl. No.: 670,716

[22] Filed: Jun. 21, 1996

[51] Int. Cl.$^6$ .................................. C07D 475/04

[52] U.S. Cl. .................. 544/257; 544/258; 544/600

[58] Field of Search .............................. 544/257

[56] References Cited

U.S. PATENT DOCUMENTS

| | | | |
|---|---|---|---|
| 4,314,988 | 2/1982 | Farina et al. | 424/1 |
| 4,337,339 | 6/1982 | Farina et al. | 544/257 |

FOREIGN PATENT DOCUMENTS 0431882  4/1990  United Kingdom.

*Primary Examiner*—Mukund J. Shah
*Assistant Examiner*—Pavanaram K. Sripada
*Attorney, Agent, or Firm*—Jerome L. Jeffers

[57] ABSTRACT

Disclosed are novel folic acid-alkaline phosphatase conjugates useful in a competitive immunoassay for folic acid in a biological fluid such as serum. A preferred conjugate involves a folate hapten bound to (N-Succinimidyl[4-iodoacetyl]aminobenzoate) through a 1,12-diamino-4,9-dioxadodecanyl spacer arm.

1 Claim, 5 Drawing Sheets

FOLATE-ALP CONJUGATE

BACKGROUND OF THE INVENTION

This invention relates to novel folic acid conjugates and to a process for their preparation.

Folic acid is a requisite cofactor in the biological transfer of carbon units at varying levels of oxidation. The measurement of folic acid and other folate cofactors or derivatives is of significant clinical value for the diagnoses of megaloblastic anemias and nutritional folate deficiencies such as those associated with alcoholism and for monitoring dosage regimens in leukemia chemotherapy. In addition, folic acid and its metabolites are potent growth promoters which are required for the reproduction of cellular genes, maturation of red blood cells and as DNA production components. Folate deficient anemia results from inadequate dietary intake, insufficient metabolic uptake or excessive utilization, usually occurring during pregnancy.

Certain automated analyzers for folic acid in serum involve a competitive protein binding assay of a labeled folic acid hapten with an antibody thereto bound to a solid support. Since the labeled hapten competes with folic acid in the serum, the magnitude of the signal derived from the labeled hapten is inversely proportional to the concentration of folic acid in the serum sample being tested. Alkaline phosphatase (ALP) is a particularly effective enzymatic label which, when the solid support bearing bound ALP labeled hapten is separated from the test sample, can be contacted with a suitable substrate to provide a colored response.

Since the labeled hapten is prepared in advance and stored in a buffered aqueous media until it is to be used by the automated analyzer, stability of the labeled hapten over extended periods of time is an essential attribute.

Gurevich et al in WO 93/17676 describe dinitrobenzoic acid derivatives, some of which incorporate the $NH_2(CH_2)_3O(CH_2)_4O(CH_2)_3NH_2$ spacer arm used in the present invention. One example shows the spacer arm coupled to folic acid to form folate $NH(CH_2)_3O(CH_2)_4O(CH_2)_3NH$-dinitrobenzoate. The dinitrobenzoic acid portion of the molecule is used for its anti-fungal activity. Nagasawa et al describe a methodology for using tBOC as an amine protecting group in Bull. Chem. Soc. Jpn., 46, 1269–1272 (1973). Levenson et al describe preparations and uses of $tBOC-NH(CH_2)_3O(CH_2)_4O(CH_2)_3NH_2$ in U.S. Pat. No. 4,803,297. The preparation of SIAB derivatized freeze-dried alkaline phosphatase and thiolation of 5' amino derivatized oligonucleotide with iminothiolane and subsequent conjugate with SIAB derivatized freeze-dried alkaline phosphatase is disclosed in EP 0 431 882 (Examples 6 and 7).

SUMMARY OF THE INVENTION

The present invention involves a folate-ALP conjugate of the formula:

(I)

wherein SIAB is (N-Succinimidyl[4-iodoacetyl] aminobenzoate) and ALP is alkaline phosphatase. Also included within the scope of the invention are intermediates necessary for preparation of the conjugate and the method of preparing the conjugate.

DESCRIPTION OF THE INVENTION

The present invention is predicated on the discovery that a folic acid-ALP conjugate in which there is a group interposed between the folic acid and ALP moieties provides increased activity and stability when compared to similar ALP conjugates of folic acid and ALP.

The conjugate of the present invention is prepared in a multistep process in which the initial step involves the preparation of folic acid-$NH(CH_2)_3O(CH_2)_4O(CH_2)_3$-NH-tBOC (where tBOC is t-butyloxycarbonyl, used here as a protecting group) by the reaction of folic acid with tBOC-$NH(CH_2)_3O(CH_2)_4O(CH_2)_3NH_2$ (prepared as described in step 1 of Example I hereof) in anhydrous dimethylsulfoxide (DMSO). This reaction gives a mixture of alpha and gamma amide products with the gamma-diasteriomer predominating (~70–80%). The alpha-diasteriomer is further, but not completely, removed during purification. DMSO is the only aprotic solvent that was found to adequately solubilize folic acid, FA-$NH(CH_2)_3O(CH_2)_4O(CH_2)_3NHtBOC$ and FA-NH $(CH_2)_3O(CH_2)_4O(CH_2)_3$-NHPDP where PDP is 3-(2-pyridyldithio)-propionate. The product of this reaction is then treated with neat trifluoroacetic acid (TFA) to remove the tBOC protecting group. The resulting amine is then reacted in DMSO with N-succinimidyl-3-(2-pyridyldithio)-propionate to provide the corresponding thiol-PDP intermediate which is reacted with dithiothreitol (DTT) to provide the functionalized folate hapten FA-$NH(CH_2)_3O(CH_2)_4O(CH_2)_3NHCOCH_2CH_2SH$. This important thiolated folate derivative is converted to the Folate-SIAB-ALP conjugate by the following method:

The enzyme, alkaline phosphatase is activated with SIAB in a basic, aqueous environment (pH 8.5-triethylaniline) to favor formation of which is then reacted with the freshly thiolated folic acid through the thiol group. The starting stoichiometry of the reactants is 5:1 hapten to enzyme. The reaction is stopped with cysteine and excess unreacted folic acid is removed on a G-25 Sephadex column. To remove any non-covalently bound folic acid, the conjugate is made 2M urea in concentration and chromatographed on another G-25 column equilibrated with 2M urea whereupon the urea is immediately removed. The conjugate is stabilized with fatty acid free BSA and preserved with azide.

This synthesis is illustrated by Scheme I.

The folate-ALP conjugate can be combined with other reagents to develop an optimized assay reagent formulation.

EXAMPLE I

Preparation of Folic Acid-SIAB-ALP Conjugate

Step 1

Synthesis of tBOC-NH(CH$_2$)$_3$O(CH$_2$)$_4$O(CH$_2$)$_3$NH$_2$

To t-Butyl-S-(4,6-dimethylpyrimidin-2yl)-thiocarbonate (35.3 g, 0.147 mmol, 0.6 equivalents) in 1,4-dioxane (100.0 mL) under argon was added dropwise via cannula, a solution of NH$_2$(CH$_2$)$_3$O(CH$_2$)$_4$O(CH$_2$)$_3$NH$_2$ (50.0 g, 0.245 mmol) in 1,4-dioxane (200.0 m) over 60 min. The reaction stirred for 24 h., was filtered of precipitated solid, and the crude product solution concentrated in vacuo under high vacuum, in a water bath at about 50° C.

The compound was purified via flash chromatography (7.5×60 cm column, 800 g of 230–400 mesh silica gel-60), eluting with 100 mL fractions of 90/20/2 (CHCl$_3$/CH$_3$OH/NH$_4$OH). Thin layer chromatography (TLC) in 90/20/2 (CHCl$_3$/CH$_3$OH/NH$_4$OH) developed an orangish colored product spot after iodine spray solution which gave an Rf value of about 0.35.

Product fractions were combined and concentrated in vacuo at about 45° C. and then dissolved into CHCl$_3$/Ether (1:1, 300 mL), washed with 50 mL water, separated, and dried with granular MgSO$_4$. The solution was filtered and concentrated in vacuo to a pale yellow product oil (~14–18 g, 40–60%).

$^1$H NMR (250 MHz, CD$_3$OD, ppm.): 1.42 (s, 9H), 1.62 (m, 4H), 1.72 (m, 4H), 1.75 (t, 2H), 3.12 (t, 2H), 3.46 (m, 8H).

Step 2

Synthesis of Folic Acid-NH(CH$_2$)$_3$O(CH$_2$)$_4$O(CH$_2$)$_3$NH-tBOC

Dicyclohexylcarbodiimide (DCC) (824 mg, 4.0 mmol, 1.3 equivalents) was added in one portion to a solution of Folic acid (1.45 g, 3.04 mmol) in anhydrous DMSO (45.0 mL, 80% into solution) under argon and in the dark, and the reaction was stirred for 0.5 h. A solution of t-BOC-NH(CH$_2$)$_3$O(CH$_2$)$_4$O(CH$_2$)$_3$NH$_2$ (912 mg mg, 3.0 mmol) in 5.0 mL anhydrous DMSO was added to the flask, dropwise via cannula over 15 minutes. The reaction stirred in the dark for 24 h. having become homogeneous after 1 hour. A white urea precipitate was filtered off after 24 hours, and the resultant clear yellow solution was concentrated in vacuo under high vacuum, at about 50° C., to provide a yellow gelatinous solid.

1 L and 3 L stock solutions of CHCl$_3$/CH$_3$OH/triethylamine (TEA), (60/15/0.5 and 60/30/1.0), labeled respectively Solvent A and Solvent B were prepared. Silica gel-60 (230–400 mesh, 325 mL volume) was added to a 350 mL coarse sintered glass funnel, set atop a 1 L vacuum filtering flask with a black rubber filtration collar, and equilibrated with Solvent A using a partial vacuum from aspirated tap water to set a steady flow rate exceeding gravity drip. After equilibration, the partial house vacuum was turned off and crude product dissolved into 6.0 mL, DMSO was evenly applied via pipette to the surface of the silica gel.

Using Solvent B, a 125 mL fraction was collected via gravity drip, followed by 125 mL fractions sequentially collected by partial vacuum (≈10–20 mm Hg) in vacuum filtering flasks. Like fractions were combined using CH$_3$OH and concentrated in vacuo to a yellow semi-solid product. High vacuum at 40° C. was then applied until complete solidification took place (750–1200 mg, 30–60%). TLC in CHCl$_3$/CH$_3$OH/TEA (30/20/1), visualizing with ceric sulfate solution, gave product as single, or as two overlapping purple colored spots, with an Rf value of about 0.5.

$^1$H NMR (250 MHz, DMSO D$_6$, ppm.): 1.35 (s, 9H), 1.50 (m, 4H), 1.58 (m, 4H), 1.8–2.3 (m, 4H), 2.95 (m, 2H), 3.08 (m, 2H), 3.3 (m, 8H), 4.3 (m, 1H), 4.56 (d, 2H), 6.63 (m, 2H), 6.65–6.95 (m, NH) 7.65 (m, 2H), 7.8–8.2 (m, NH's) 8.63 (s, 1H). $^{13}$CD NMR (250 MHz, DMSO D$_6$, ppm.): 26.05 (2-methylene), 28.29 (tBOC), 29.4 (methylene), 29.8 (methylene), 35.8 (methylene), 37.3 (methylene), 45.98 (methylene, 53.0 (methine), 67.7 (2-methylene), 69.84 (2-methylene), 111.2 (CH, arom.), 111.3 (CH, arom.), 128.6 (CH, arom.), 129.1 (CH, arom.), 148.5 (CH, arom.). FAB/MS: 728.4 (M+H), 629.4 (-tBOC), 295.2 (BASE). IR: (KBr, CM$^{-1}$): 3700, 3300, 2933, 2857, 1700, 1645, 1610, 1520, 1370, 1250, 1180, 1110, 1030.

Step 3

Synthesis of Folic Acid-NH(CH$_2$)$_3$O(CH$_2$)$_4$O(CH$_2$)$_3$NH$_2$

To FA-NH(CH$_2$)$_3$O(CH$_2$)$_4$O(CH$_2$)$_3$NH-tBOC (300.0 mg, 413 mmol) in an aluminum foil wrapped, tared 25 mL flask, under argon and in the dark, was added 2.0 mL anhydrous TFA. The reaction was stirred for 1 h. and the stir bar was then removed. Concentration in vacuo under high vacuum at 45° C., with an aluminum foil shield covering the flask and bath, provided a viscous oil/semi-solid which was chilled in an ice bath for 5 min.

The residue in the flask was then tritrated with CH$_2$Cl$_2$ (3×10 mL) and stirred with a small spatula to provide solid product which was dried under high vacuum at 35° C., using an aluminum foil shield to cover the flask and bath. Any solid clumps of product were then broken up and the flask was wrapped in aluminum foil, with high vacuum re-applied at 25° C. for 1 h. The tared flask plus product was weighed, the flask was stoppered, and then purged with argon. The calculated product weight, typically ~325 mg (125%), corresponded to an excess of the theoretical yield, as TFA salt formation accounted for at least part of the product yield.

TLC in CHCl$_3$/CH$_3$OH/TEA (30/20/1), visualizing with ceric sulfate solution, gave product that appeared as a single spot, or as two overlapping purple colored spots with an Rf of about 0.06, showing complete spot to spot conversion from starting material.

$^1$H NMR (250 MHz, DMSO D$_6$, ppm.): 1,14 (m, 4H), 1.59 (qr. 2H), 1.75 (quint. 2H), 2.1–2.3 (dt, 4H), 3.32 (m 6H), 3.4 (t, 2H), 4.32 (m, 1H), 4.5 (s, 2H), 6.63 (d, 2H), 7.35 (m, NH), 7.65 (d, 2H), 7.8 (t, NH), 7.92 (d, NH), 8.18 (d, NH), 8.64 (s, 1H). $^{13}$CD NMR (250 MHz, DMSO D$_6$, ppm.: 26.0 (2-methylene), 27.3 (methylene), 29.4 (methylene), 30.7 (methylene), 31.9 (methylene), 35.9 (methylene), 36.8 (methylene), 45.9 (methylene), 52.6 (methine), 66.9 (methylene), 67.7 (methylene), 69.8 (methylene), 69.9 (methylene), 111.2 (2-CH, arom.), 128.99 (CH, arom.), 129.1 (CH, arom.), 148.4 (CH, arom.), 177. (C=O), 191. (C=O). FAB/MS: 650 (M+Na), 628 (M+H), 154 (BASE). IR: KBr, cm$^{-1}$): 3380, 2950, 1715, 1645, 1610 1510, 1440, 1385, 1330, 1190, 1140, 945, 840, 800, 710.

Step 4

Synthesis of Folic Acid-NH(CH$_2$)$_3$O(CH$_2$)$_4$O(CH$_2$)$_3$NHCOCH$_2$CH$_2$SSPyr[1]

[1] Pyr refers to the pyridine portion of the SPDP reagent.

To FA-NH(CH$_2$)$_3$O(CH$_2$)$_4$O(CH$_2$)$_3$NH$_2$ (0.412 mmol) in an aluminum foil wrapped, tared 25 mL flask, under argon, was added anhydrous DMSO (10.0 mL). The mixture was stirred under argon and in the dark for 20 min., while reagent dissolved into solution. TEA (172 µL, 1.24 mmol, 3 eq.) was then added to the flask via syringe, followed by N-Succinimidyl-3-(2-pyridyldithio)-propionate (SPDP) (129.0 mg, 0.412 mmol) in one portion. After the reaction stirred in the dark under argon for 16–24 h, the stir bar was removed and the reaction was concentrated in vacuo under high vacuum at 50° C. with an aluminum foil shield over the flask and bath. A viscous oil/semi-solid formed in the flask, which was then chilled in an ice bath for 5 min.

This residue was then titrated with $CH_2Cl_2$ (2×20 mL) and stirred with a small spatula to provide solid product which was filtered, and dried under high vacuum at 35° C. using an aluminum foil shield to cover the flask and bath. Any solid clumps of product were then broken up and the flask was wrapped in aluminum foil, with high vacuum re-applied at 25° C. for 1 h. The weight of the product was calculated, typically about 160–225 mg (48–65%), and the sample purged with argon.

TLC in $CHCl_3/CH_3OH/NH_4OH$ (60/40/10), visualizing with a solution of aqueous iodine followed by a solution of ceric sulfate, produced faint orange tinted spots with an Rf of about 0.4 for the new product as either a single spot or as two overlapping spots. Orange spots for the starting material had an Rf value of about 0.2.

Final Purification: DMSO (1 mL/125 mg product) was added to the amber glass product vial, and stirred well to dissolve the product. (Warm at 40° C. if necessary.) The solution was poured into a 10 mL beaker and distilled water added (2 mL/125 mg product) to give a yellowish precipitate.

The product was collected by vacuum filtration, washed with water (2×1.0 mL), placed into a tared amber glass vial, and then dried under high vacuum at about 35° C., for about 15 minutes. Any solid clumps of the yellowish product were broken up and high vacuum was reapplied for at least 2 hours. The tared vial plus product was weighed and then the weight of the product calculated. Typically this value was 140–225 mg over several runs with the higher yields being obtained during later runs when conditions were standardized. Before storing, the vial was purged with argon.

$^1$H NMR (250 MHz, DMSO $D_6$, ppm.): 1.44 (m, 4H), 1.6 (m, 4H), 1.75–2.1 (m, 4H), 2.2 (dt, 4H), 2.9–3.15 (m, 4H), 3.32 (m, 8H), 4.3 (m, 1H), 4.48 (s, 2H), 6.65 (d, 2H), 6.9 (m, NH), 7.21 (dt, NH, pyr), 7.65 (d, 2H), 7.7–8.15 (m, NH's), 8.18 (d, NH, pyr), 8.45 (d, NH, pyr), 8.63 (s, 1H). $^{13}$CD NMR (250 MHz, DMSO $D_6$, ppm.): 26.1 (2-methylene), 29.42 (2-methylene), 30.6 (methylene), 32.1 (methylene), 34.2 (methylene), 34.6 (methylene), 35.9 (2-methylene), 45.99 (methylene-NH) 52.8 (methine), 67.6 (2-methylene), 69.9 (2-methylene), 111.2 (2-CH, arom.), 119.2 (CH, pyr.), 119.9 (CH, pyr.), 120.2 (CH, pyr.), 129.0 (CH, arom.), 129.1 (CH, arom.), 137.8 (CH, pyr.), 148.6 (CH, arom). FAB/MS: 825.6 (M+H), 307 (BASE, matrix). IR: (KBr, $cm^{-1}$): 3700–2400, 1710, 1650, 1540, 1415, 1350, 1195, 1130, 840, 770, 720.

Step 5

Synthesis of Folic Acid-$NH(CH_2)_3O(CH_2)_4O(CH_2)_3NHCOCH_2CH_2SH$

To FA-$NH(CH_2)_3O(CH_2)_4O(CH_2)_3$NH-PDP (5.00 mg 0.0069 mmol) in an amber glass vial, under argon in the dark, was added anhydrous DMF (500 µL) with stirring for 10 min. In addition to the argon flush line, a syringe tipped argon purge line was inserted into the reaction vial and argon gently bubbled directly through the DMF solution. (Caution: A vigorous argon purge stream will cause DMF evaporation and reagent precipitation.) The solution was degassed for 30 min., and the purge line maintained throughout the course of the reaction.

DTT (0.90 mg, 0.95 equiv., 0.0058 mmol) was then added in one portion, the vial resealed with a new septum, both argon purge lines reinserted, and the reaction stirred for 2 h. The formation of FA-$NH(CH_2)_3O(CH_2)_4OCH_2)_3NHCOCH_2CH_2SH$ was verified by TLC in $CHCl_3/CH_3OH/NH_4OH$ (60/40/10), visualized with aqueous iodine followed by ceric sulfate spray solution. The product spot (Rf of about 0.25) appeared very faintly as a single, or two closely overlapping spots about 0.15 Rf units below a faint residual starting material spot (0.05 equiv. excess with an Rf of about 0.4).

Argon lines were removed, and the vial was wrapped with parafilm. The maximum theoretical product concentration was based on the quantity of DTT used and the volume of DMF. Thus, 0.0058 mmol/0.500 mL=0.0116 mmol/mL (11.6 nM/µL). The in situ-generated product solution was then ready to be vended.

Step 6

Synthesis of Folic Acid-$NH(CH_2)_3O(CH_2)_4O(CH_2)_3NHCOCH_2CH_2S$-SIAB-ALP

Start with approximately 73 mg (5 mL) of Biozyme Alkaline Phosphatase 12 G (14.7 mg/mL) and buffer exchange into (100 mM Triethanolamine; 100 mM NaCl; 1 mM EDTA; pH 8.5, containing 1 mM $MgCl_2$). Concentrate to 7–8 mg/mL. Activate with SIAB at 20:1 molar excess SIAB:ALP for 25 minutes at room temperature. Make a 20 nmole/µL (8.04 mg/mL) solution of SIAB in DMF. Determine that total nmoles of enzyme by multiplying mg ALP× 7.52. Then determine nmoles of SIAB by multiplying nmoles of enzyme by 20. Divide nmoles of SIAB needed by 20 nmoles/µL solution and add µL of SIAB to enzyme. This is always around 5% of volume, so that DMF final concentration in solution is not too high so as to inactivate the antibody.

This reaction incubates without stirring at room temperature for 25 minutes. After this incubation, the reaction is stopped by quenching with a 12M excess of glycine. The nmoles of SIAB added are multiplied by 0.012 to give the µL of a 1M glycine solution needed to stop the reaction. This reaction sits for another 4 minutes and is then chromatographed on a G-25 Sephadex column.

A conjugate of this size requires 4 PD-10's (Pharmacia pre-poured G-25 Sephadex column) equilibrated in TSE, pH 8.5, with 1 mM $MgCl_2$. The activated enzyme is eluted in the void. Instead of collecting the full 3.5 mL void, only 3.0 mL is taken so as to prevent potential contamination of the activated enzyme with any small molecular weight material (e.g. SIAB, glycine).

This pool of activated antibody is analyzed for protein content by UV absorbance at 280 nm. Approximately 11.5 mL is obtained at 9 mg/mL, thus giving an apparent yield of 142%. This occurs because the SIAB group on the enzyme gives the enzyme a higher extinction coefficient. In the following calculations, the normal extinction coefficient of 1.0 is used even for the SIAB activated molecule.

This activated enzyme is then reacted with freshly thiolated folic acid stored under argon. For 18 mg of activated enzyme, 58 µL of 11.6 nM/µL thiolated folic acid is needed to make a 5M excess of folic acid to enzyme. Prior to addition to enzyme, the folic acid solution is made 1 mM $MgCl_2$ by the addition of 1 µL/mL of 1M $MgCl_2$.

This reaction is allowed to sit at room temperature for two hours with gentle mixing. After incubation, the reaction is stopped with a 12M excess of 1M cysteine. The nmoles of thiofolate are multiplied by 0.012 to yield the μL of 1M cystein needed to be added.

Then the conjugate reactants are separated on another set of G-25 columns again collecting only 3.0 mL of a possible 3.5 mL void volume off of a PD-10 column. This series of instructions are completed in a single day and the conjugate may be placed at 2°–8° C. overnight.

The next day, G-25 columns are equilibrated in TSMZ (100 mM Triethanolamine, 100 mM NaCl, 1 mM MgCl$_2$, 0.1 mM ZnCl$_2$, pH 7.3) containing 2M urea. The conjugate solution is made 2M by diluting equal amounts with TSMA/ 4M urea. Then the void volume of 3.0 mL (from a potential 3.5 mL of a PD-10/NAP Pharmacia G-25) is collected.

This conjugate solution is immediately buffer exchanged away from the urea into straight TSMZ. Small samples for protein analysis are removed and the remaining conjugate is made 0.5% with fatty acid free bovine serum albumin (BSA). Azide is added to 0.1% and the conjugate is stored at 2°–8° C. protected from light.

EXAMPLE II

Other conjugate linkers were attempted to provide a stable hapten-enzyme conjugate.

Initially, a N-Succinimidyl S-Acetylthioacetate (SATA) derivative of the folic intermediate acid was prepared. This was deacetylated with hydroxylamine after dissolving in DMF. Then this deacetylated SATA-folic acid was reacted with a succinimidyl 4-[N-maleimidomethyl]cyclohexane-1-carboxylate (SMCC) activated ALP 12 G (introduction of maleimide). This chemistry did not provide a stable conjugate even after several attempts to fine-tune the hapten loading and controlling the reaction with glycine stops.

An N-Succinimidyl-3-(2-pyridyldithio)propionate (SPDP) derivative of folic acid was then prepared to produce a hapten conjugate. This same folic acid derivative was cleaved with DTT and was then linked to alkaline phosphatase through a SIAB group introduced on the enzyme as in Example I. This conjugate had the desired performance capability.

EXAMPLE III

Synthesis of NHS Conjugates

Preparation of Folic Acid NHS Ester—Folic acid (25.7 mg, 0.058 mmol) was dissolved in 0.8 mL of DMSO in a conical vial containing a stir bar. Dicyclohexylcarbodiimide (DCC) (36.8 mg, 0.178 mmol) was dissolved in 0.3 mL of DMF. To this solution was added 20.8 mg, 0.181 mmol of N-hydroxysuccinamide (NHS). After the NHS dissolved, this solution was added to the flask containing the folic acid solution in three separate portions while stirring. The reaction was stirred for 20 hours in the dark at room temperature, during which time a white precipitate formed. After filtration to remove the precipitate there resulted a clear yellow solution.

Preparation of Folate—ALP—10 mg of ALP in 2 mL of 0.05M Tris buffer, 1 mM magnesium chloride, 0.1 mM zinc sulfate (pH 7.6). Folate NHS ester (0.2 mL) was added in 0.05 mL portions to the stirring formulation. The resulting cloudy solution was stirred at room temperature in the dark for 16 hours and then stirred at 2°–8° C. for another 24 hours. The conjugate was then purified by chromatography on a 1.8×40 cm column of Sephadex G-25 equilibrated with 0.05M sodium borate, 2M urea (pH 9.5). The protein peak was concentrated to 0.5 mL by ultrafiltration and chromatographed a second time on the Sephadex G-25 column. The protein fraction was then concentrated by ultrafiltration and the buffer was exchanged to 0.05M Tris, 1 mM MgCl$_2$, 0.1 mM ZnSO$_4$ (pH 7.6).

EXAMPLE IV

Folate Assay Using Magnetic Separation

The folate-alkaline phosphatase conjugates prepared as described above were used as a tracer in a heterogenous competitive magnetic separation assay in the commercially available Technicon Immuno 1® analyzer. All reaction steps were performed at 37° C. with the analysis being carried out in two steps. During the first step, the test sample (60 μL) was first contacted with 50 μL of 5 mM dithiothreitol. After 15 minutes, 50 μL of sodium hydroxide was added with 35 minutes of continued incubation. This pretreatment step is for the purpose of releasing folate from endogenous binding proteins. During the second step, the pretreated test sample containing the released folate was reacted with 80 μL of a buffered solution of fluoresceinated folate binding protein (400 μg/mL) which reduced the pH to approximately 9.5. After 15 minutes, 50 μL of folate-ALP conjugate (1 μg/mL) was added which competes with folate contained in the sample for binding sites on the folate binding protein. Monoclonal Immuno Magnetic Particle (mIMP™) reagent (20 μL) consisting of paramagnetic microparticles with monoclonal anti-fluorescein antibodies covalently attached to their surface were then added. The reaction was then incubated for 8 minutes during which time the fluorsceinated folate binding protein bound to the mIMP™ reagent. The mIMP-binding protein complex was washed to remove unbound materials after which para-nitrophenyl phosphate (pNPP) substrate was added. The alkaline phosphatase in the bound folate-ALP conjugate reacts with the pNPP to form colored paranitrophenoxide and phosphate. The rate of increase in absorbance at 405 nm ($A_{405}$/min) due to formation of para-nitrophenoxide was monitored by U.V. absorption. A sample containing no folate will exhibit maximum bound label while a sample having haigh folate concentration will have bound minimal label. Thus, the measured reaction rates are inversely proportional to the folate concentration in the sample.

Standard curves were constructed using calibrators containing known concentrations of folic acid. The curves were normalized by comparing the reaction rate (B) at a given folate concentration to the reaction rate ($B_o$) in the absence of folate and % $B/B_o$ was plotted against folate concentration. Folate concentrations in test samples were quantified by comparing reaction rates against this standard curve.

The activities of the NHS, SATA-SMCC and SPDP-SIAB conjugates were compared by measuring $B_o$ (the reaction rate using zero calibrator as sample) at various conjugate concentrations. The SATA-SMCC and SPDP-SIAB conjugates had higher specific activities than the NHS conjugates, yielding higher $B_o$ rates per mass of protein added to the reaction mixture. Both SATA-SMCC and SPDP-SIAB conjugates yielded the desired $B_o$ reaction rates of 0.5 to 0.9 $A_{405}$/min at concentrations of approximately 0.5 to 1 μg/mL. To achieve these reaction rates, NHS conjugate concentrations of approximately 1 to 5 μg/mL were required. At 5 μg/mL, which was a typical loading for NHS conjugates, the SATA-SMCC conjugate produced reaction rates which were too high to be measured by the Technicon Immuno 1® analyzer.

TABLE 1

Comparison of $B_0$ Reaction Rates of Folate-ALP Conjugates

| Conjugate Concentration (μg/mL) | Reaction Rate ($A_{405}$/min) | | |
|---|---|---|---|
| | NHS Conjugate | SATA-SMCC Conjugate | SPDP-SIAB Conjugate |
| 0.5 | ND[a] | 0.559 | 0.471 |
| 1 | 0.545 | 0.921 | 0.835 |
| 5 | 0.938 | >2[b] | 1.620 |

[a]Not determined.
[b]Reaction rate too high to measure.

BRIEF DESCRIPTION OF THE DRAWINGS

Figure 1:
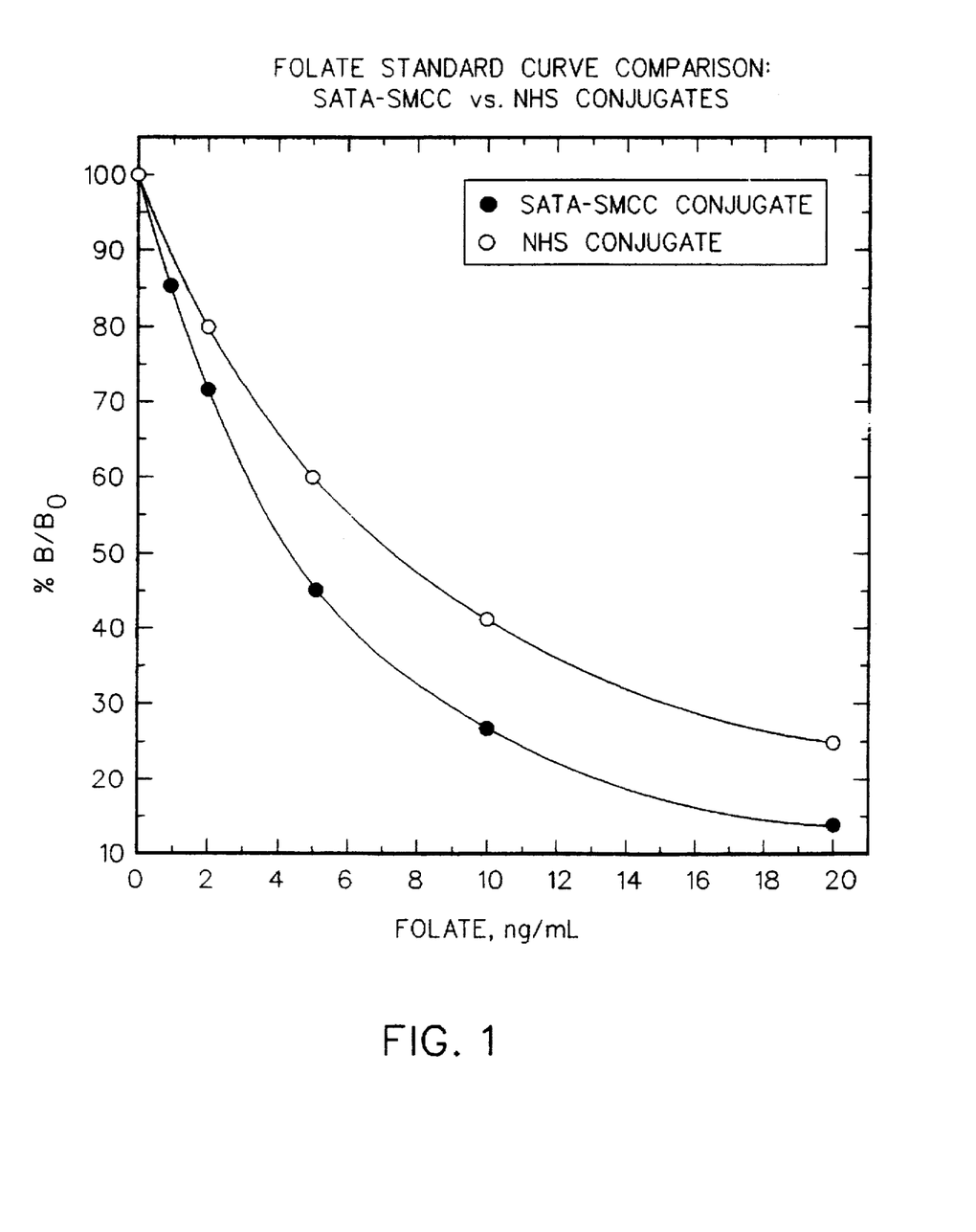

The sensitivities of the SATA-SMCC, SPDP-SIAB and NHS folate conjugates were also compared. In the assay described herein, the measurement of exogenously added folate from a sample is dependent on its ability to displace the folate ALP from the folate binding protein. A conjugate which is displaced more easily from the folate binding protein will produce a larger change in reaction rate per unit of exogenously added folate. The SATA-SMCC and SPDP-SIAB conjugates performed equivalently in the folate assay described herein. Both conjugates showed greater displacement than NHS conjugates from folate binding protein by exogenously added folate. The SATA-SMCC conjugate exhibited 50% displacement at 4 mg/mL folate as compared with 7 mg/mL folate for the NHS conjugate as illustrated by FIG. 1.

Figure 2:
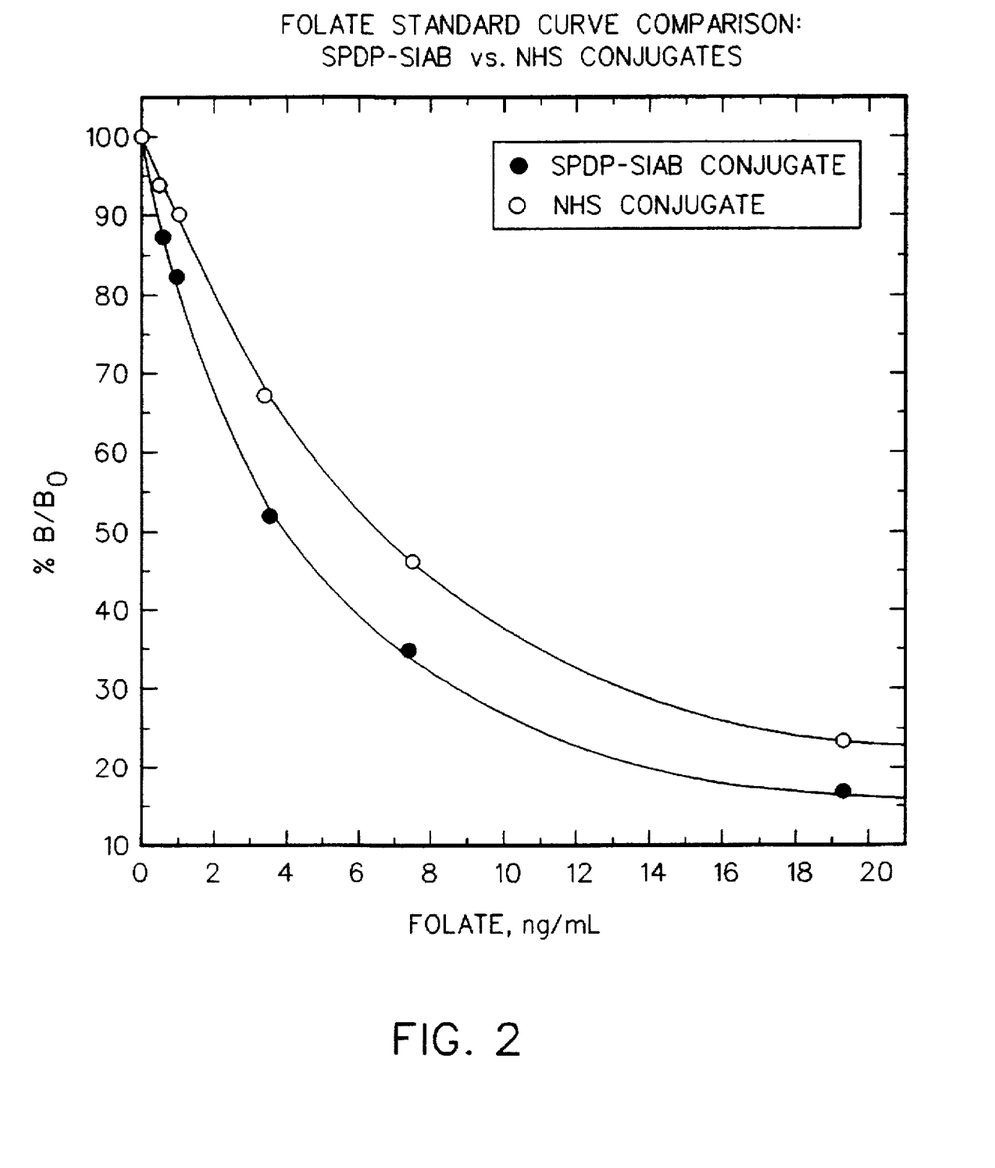

In a separate study, the SPDP-SIAB conjugate exhibited 50% displacement at 4 ng/mL compared with 6.4 ng/mL for the NHS conjugate (FIG. 2). This resulted in better sensitivity (difference in reaction rates at low folate concentrations) and dynamic range difference (difference in reaction rates across the entire calibration curve analyte range) when the SATA-SMCC or SPDP-SIAB conjugates were used in the folate assay than when the NHS conjugate was used.

Figure 3:
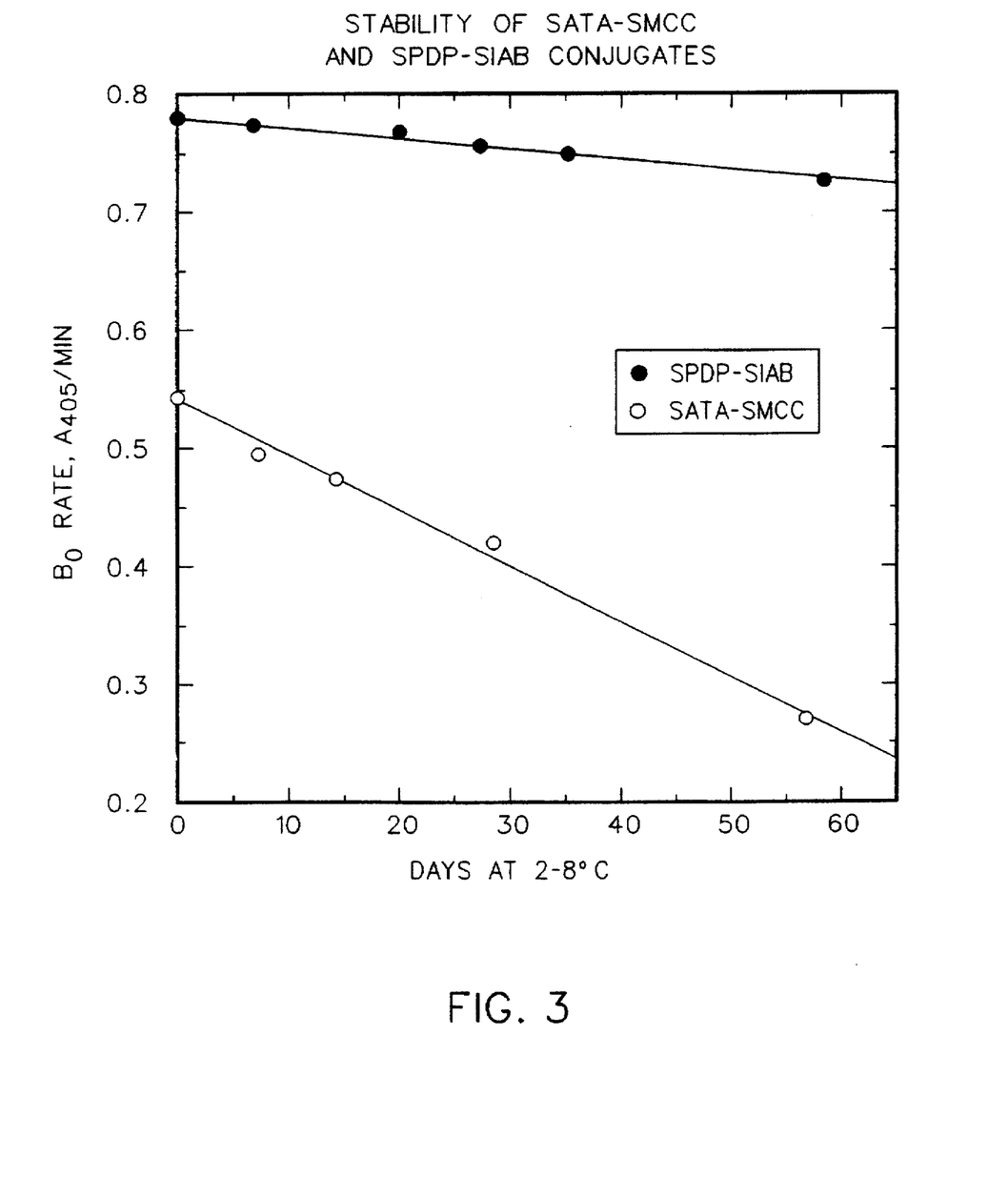
Figure 4:
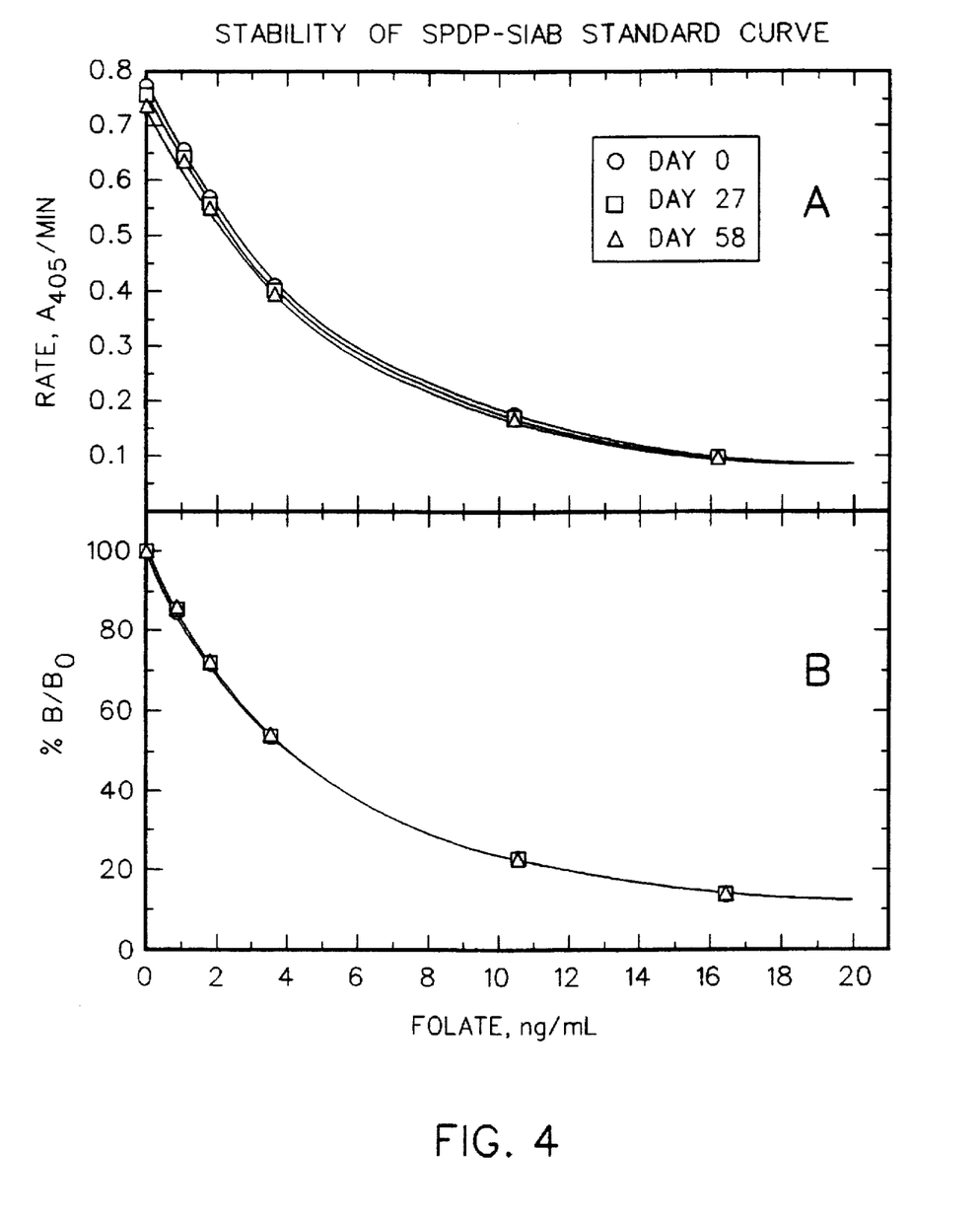
Figure 5:
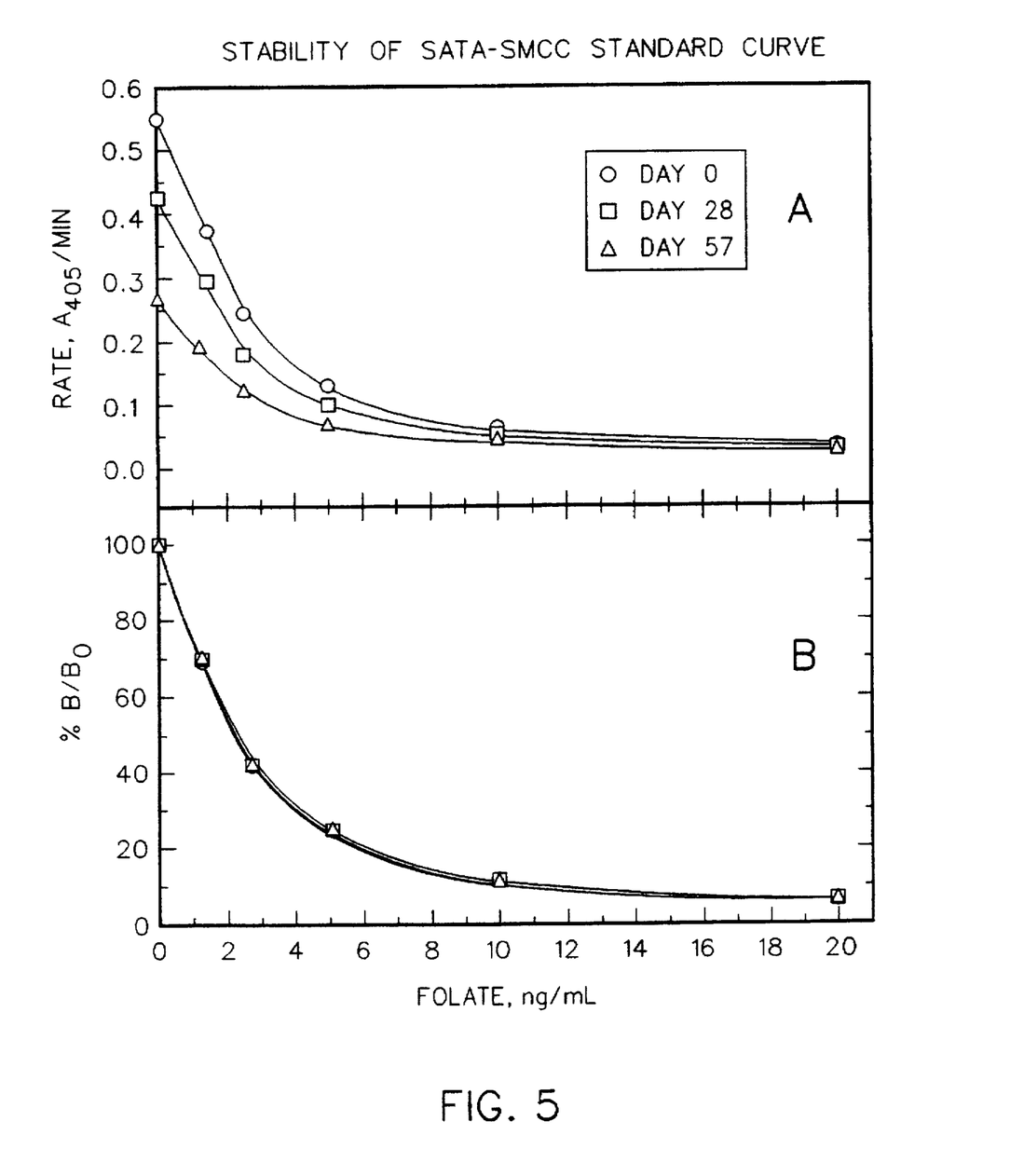

Stability of the conjugates was determined by measuring the change in $B_0$ rates over time. FIG. 3 shows that the SPDP-SIAB conjugate has superior stability to the SATA-SMCC conjugate. Over an eight week period, the SPDP-SIAB $B_0$ rates decreased by 50%. To determine if the decrease in rates would affect assay performance, the stabilities of standard curves were measured. Standard curves obtained with the SPDP-SIAB conjugates expresses as absolute rates (FIG. 4A) or % $B/B_0$ (FIG. 4B) changed little over an eight week period. Standard curves obtained with the SATA-SMCC conjugates showed a decrease in reaction rates across the entire standard curve range over the same time period (FIG. 5A). FIG. 5B shows that the shape of the standard curve, expressed as % $B/B_0$, does not change over the period indicated although the absolute reaction rates decrease.

The SPDP-SIAB conjugate exhibited superior stability to the SATA-SMCC conjugate. The decrease in reaction rates observed with the SATA-SMCC conjugate is most likely due to the breakdown of the maleimide linkage between the SATA and SMCC moieties. If SATA-SMCC conjugates were to be used, the decrease in absolute rates would require more frequent calibration.

What is claimed is:

1. A folic acid-alkaline phosphatase conjugate of the formula:

where SIAB is (N-Succinimidyl[4-iodoacetyl]aminobenzoate) and ALP is alkaline phosphatase.

* * * * *